United States Patent [19]

Jarvik et al.

[11] Patent Number: 4,832,051
[45] Date of Patent: May 23, 1989

[54] MULTIPLE-ELECTRODE INTRACOCHLEAR DEVICE

[76] Inventors: Robert K. Jarvik, 5974 Holladay Blvd., Salt Lake City, Utah 84121; Patrick K. Campbell, 1439 Roxbury Rd., Salt Lake City, Utah 84108

[21] Appl. No.: 879,839

[22] Filed: Jun. 27, 1986

Related U.S. Application Data

[63] Continuation of Ser. No. 728,307, Apr. 29, 1985, abandoned.

[51] Int. Cl.⁴ .............................................. A61N 1/04
[52] U.S. Cl. ................................. 128/784; 128/420.6
[58] Field of Search ................... 128/419 R, 783, 784, 128/786, 791, 420.5, 420.6

[56] References Cited

U.S. PATENT DOCUMENTS

| | | | |
|---|---|---|---|
| 3,474,791 | 10/1969 | Bentov | 128/786 |
| 3,516,412 | 6/1970 | Ackerman | 128/786 |
| 3,825,015 | 7/1974 | Berkovits | 128/786 |
| 4,000,745 | 1/1977 | Goldberg | 128/785 |
| 4,284,856 | 8/1981 | Hochmair et al. | 128/420.6 |
| 4,437,474 | 3/1984 | Peers-Trevarton | 128/784 |

FOREIGN PATENT DOCUMENTS

| | | | |
|---|---|---|---|
| 7157 | 1/1980 | European Pat. Off. | 128/784 |
| 2823798 | 9/1979 | Fed. Rep. of Germany | 128/784 |
| 2421626 | 12/1979 | France | 128/786 |
| 48312 | 12/1983 | World Int. Prop. O. | 128/784 |

*Primary Examiner*—William E. Kamm

[57] ABSTRACT

A cochlear electrode device having the properties of axial stiffness and lateral flexibility and comprising a plurality of substantially incompressible, flat elements, with the elements being assembled adjacent and in contact with one another along a common axis to form a stack and with the elements being resiliently atached together so that the stack of elements is stiff in compression along the common axis and is flexible in tension when the elements are forced to deviate from the common axis by the application of an external force. A plurality of electrodes and connecting wires are supported by the stack at spaced apart locations along its length.

24 Claims, 8 Drawing Sheets

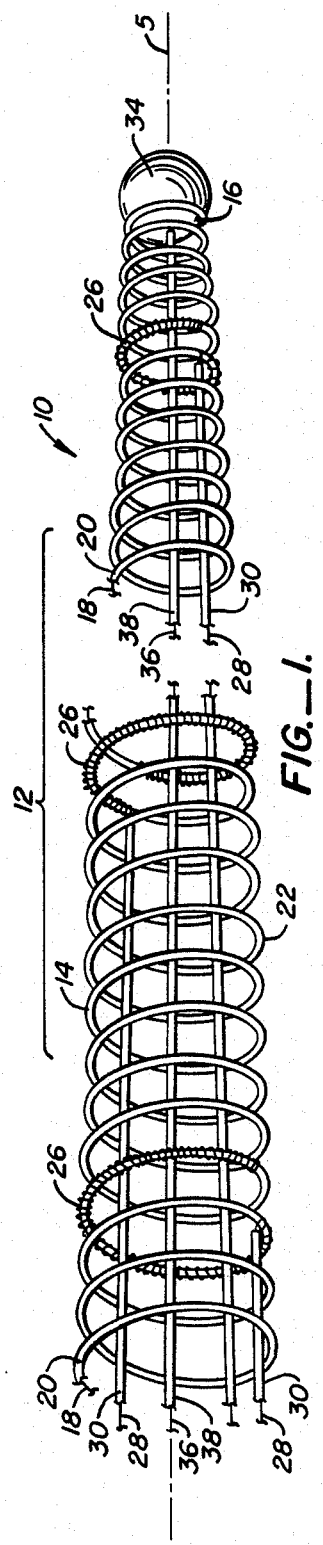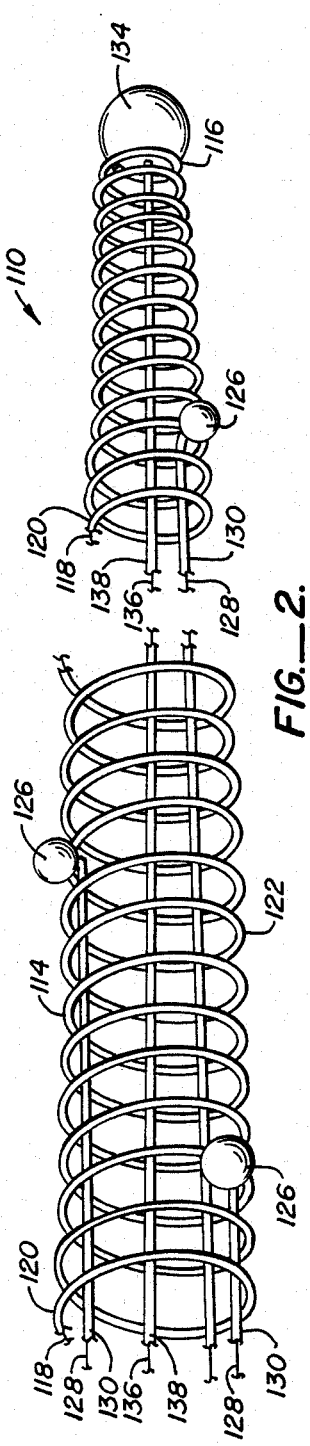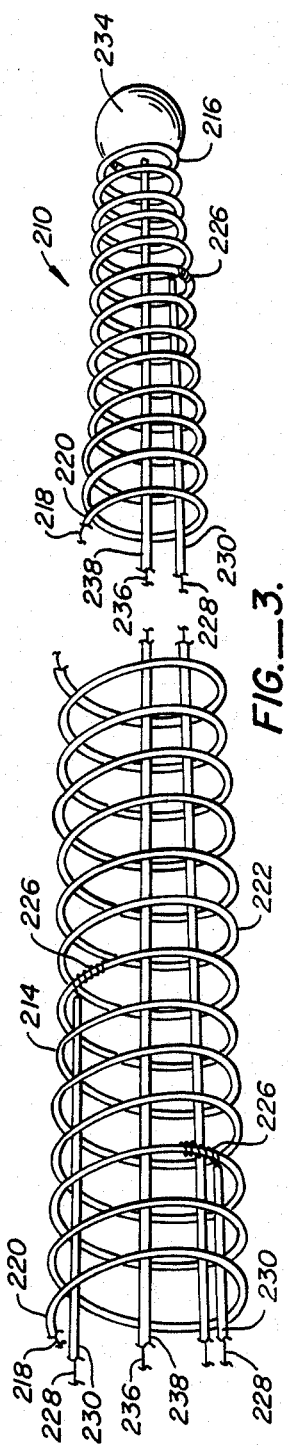

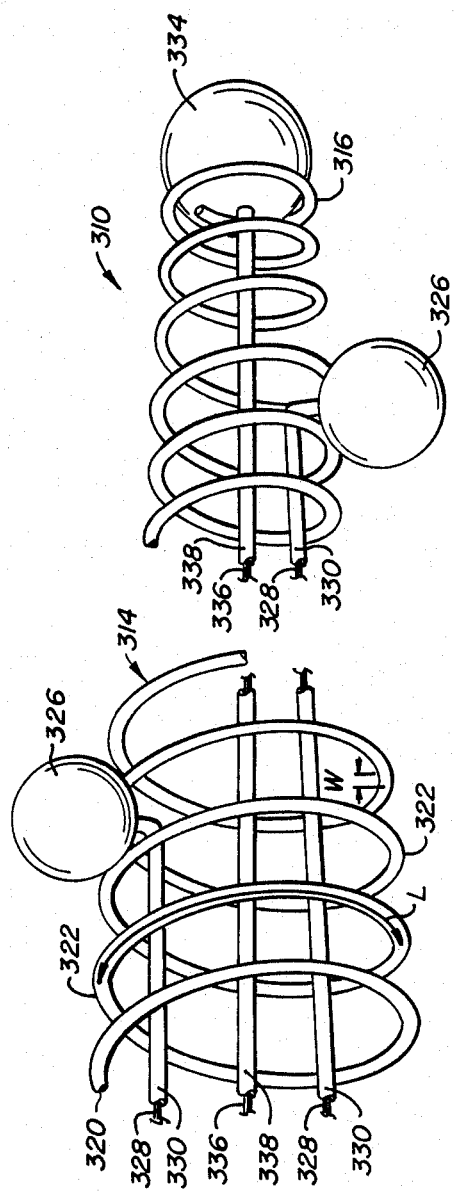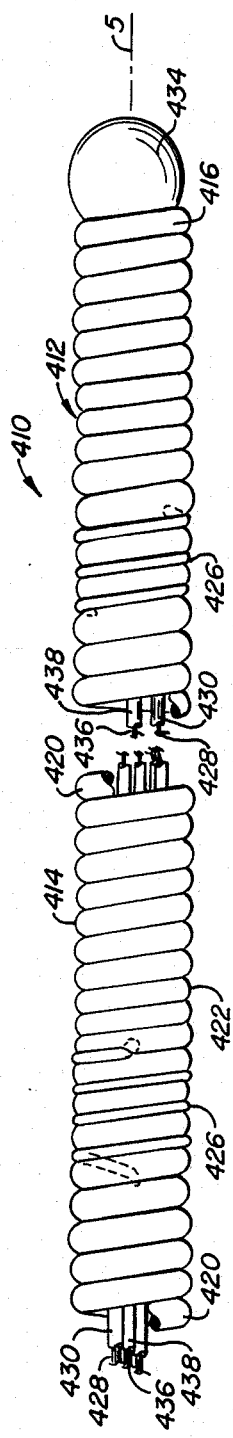
FIG._4.
FIG._5.

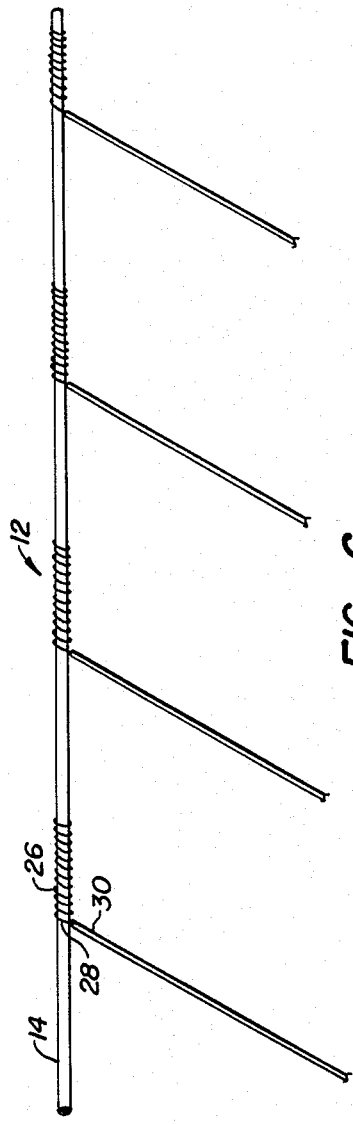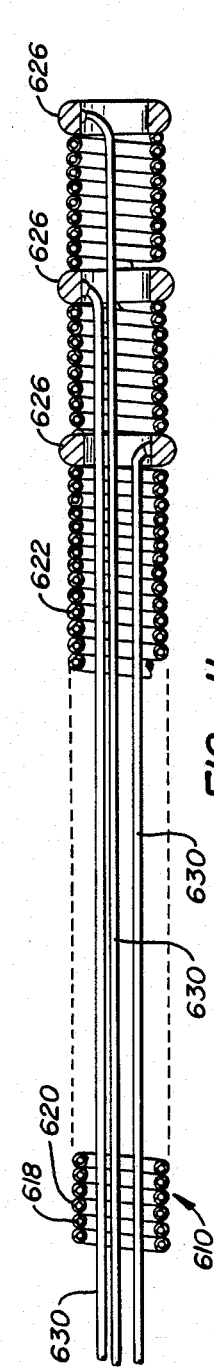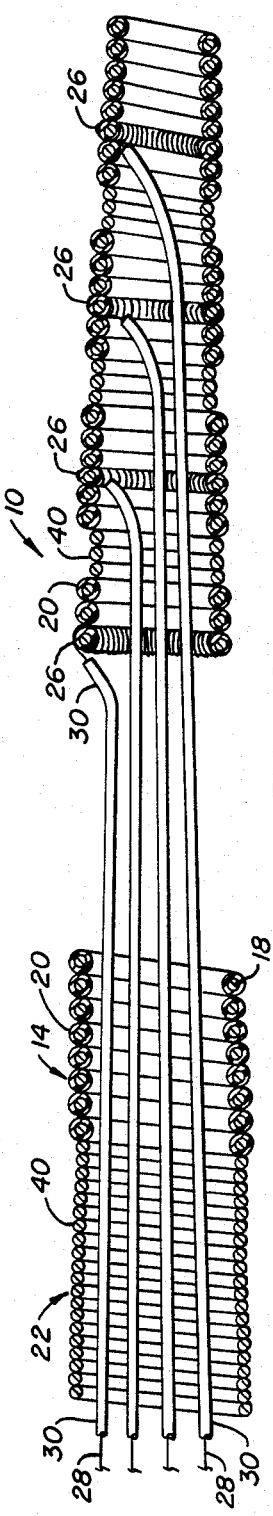
FIG._6.  FIG._11.  FIG._12.

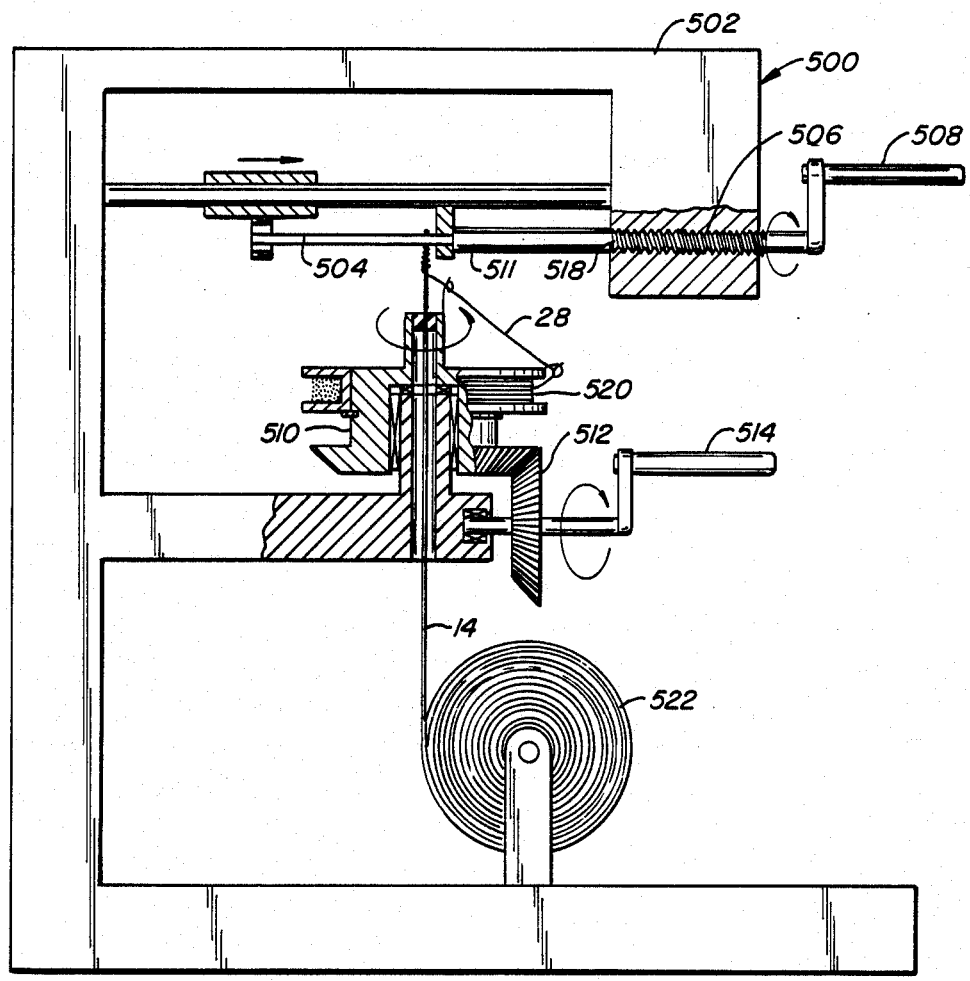
FIG._7.
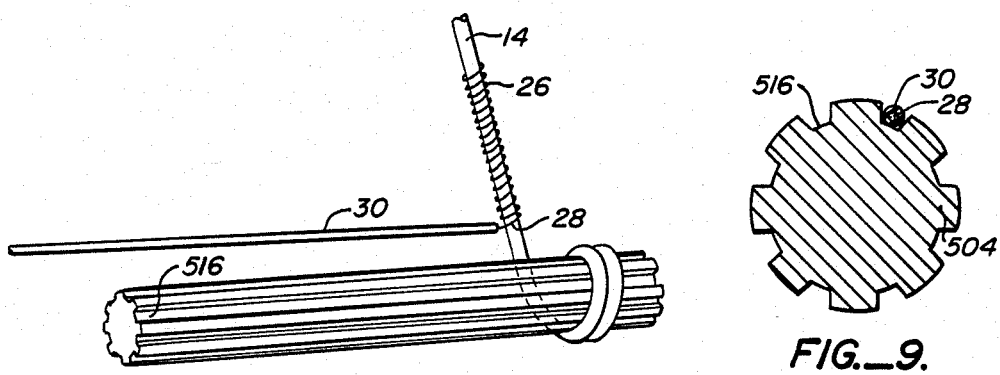
FIG._8.
FIG._9.

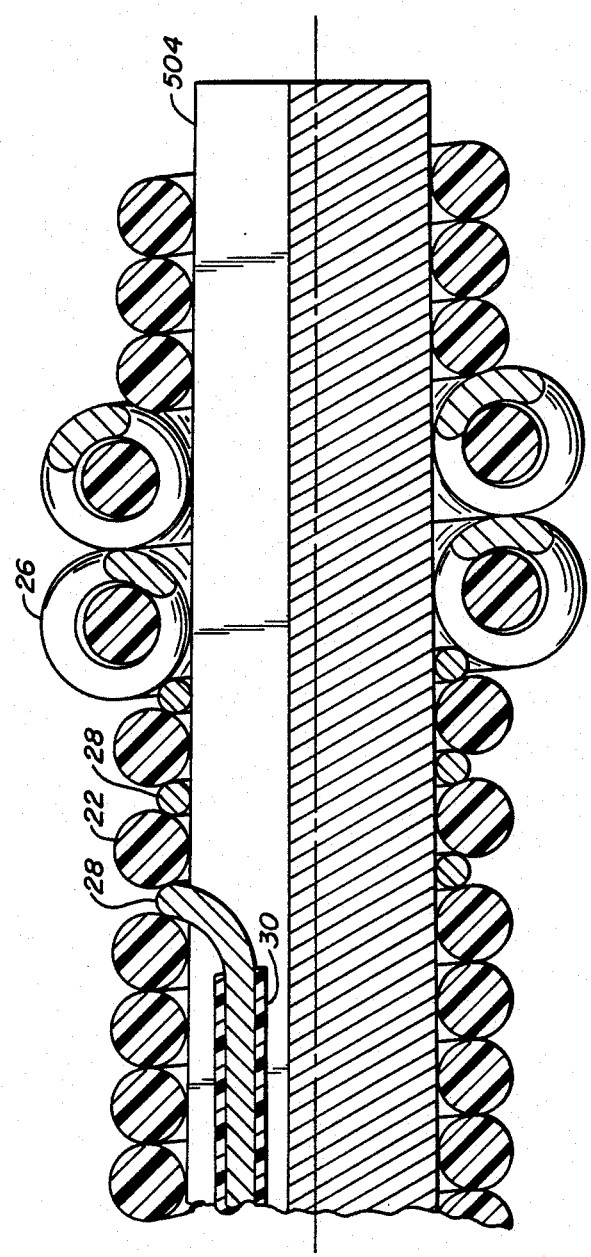
FIG._10.
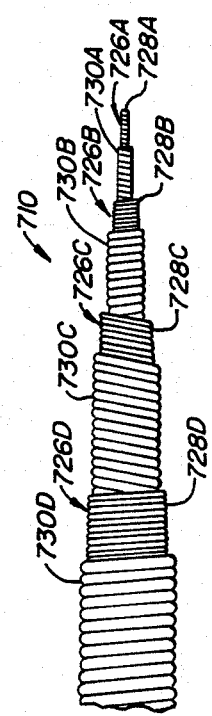
FIG._13.

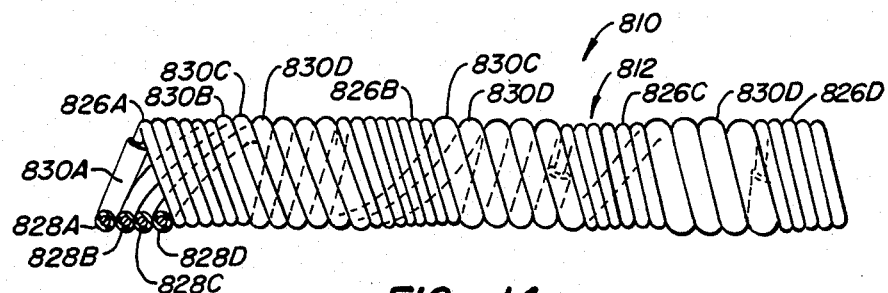
FIG._14.
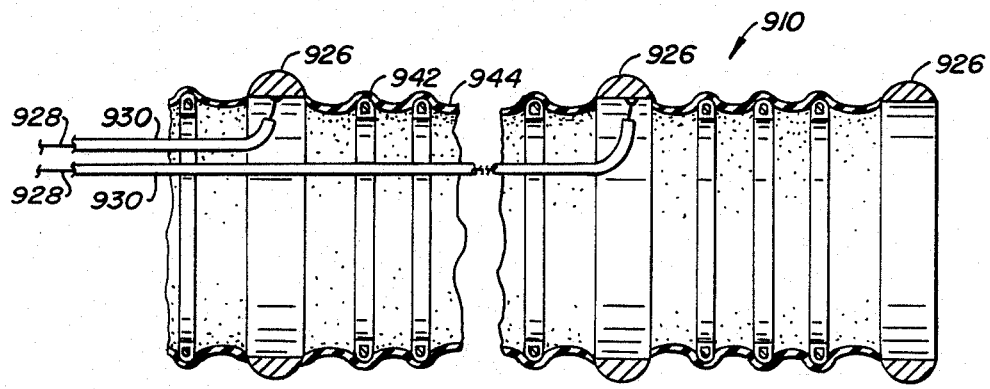
FIG._15.

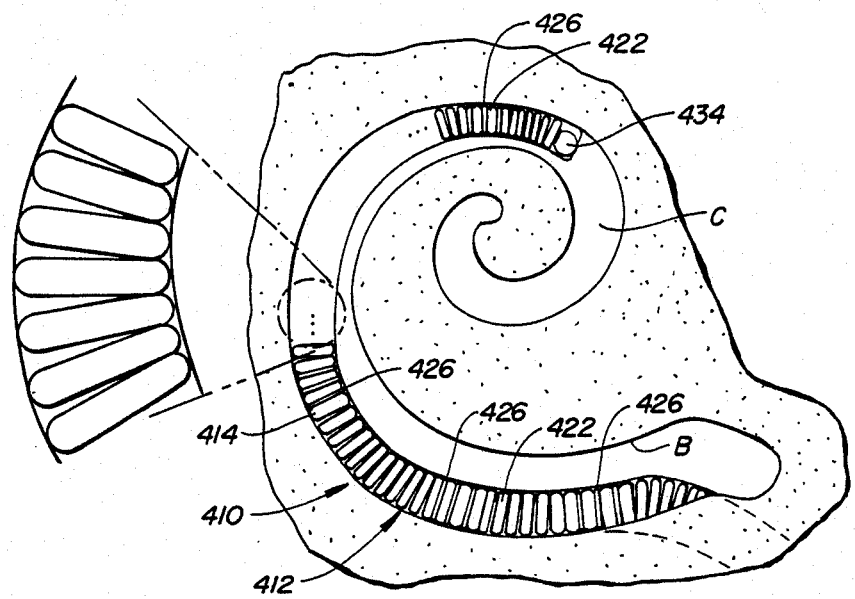
FIG.—16.
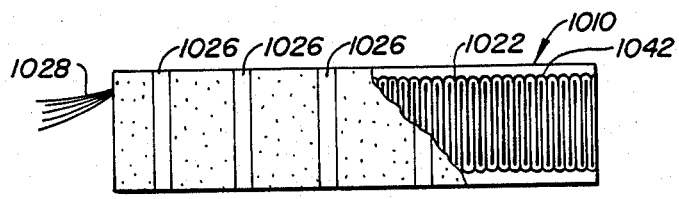
FIG.—17.
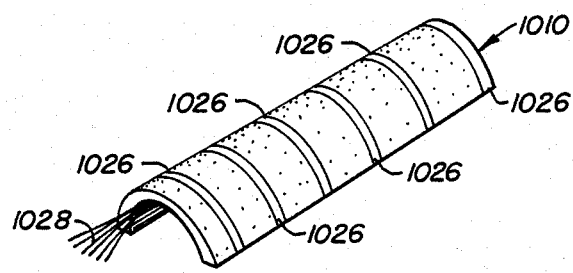
FIG.—18.
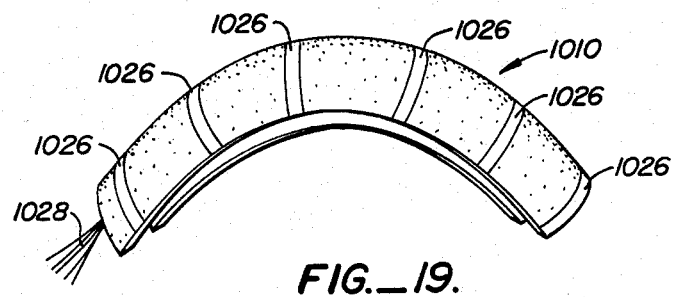
FIG.—19.

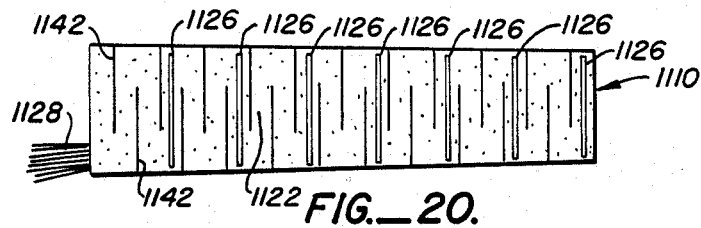
FIG._20.
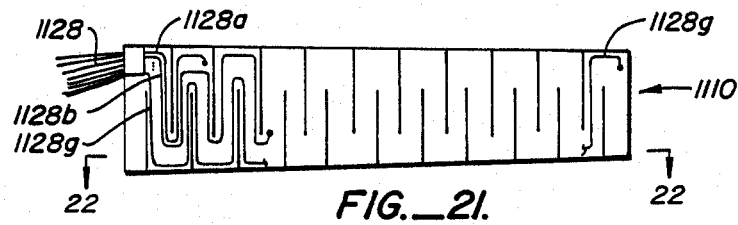
FIG._21.
FIG._22.
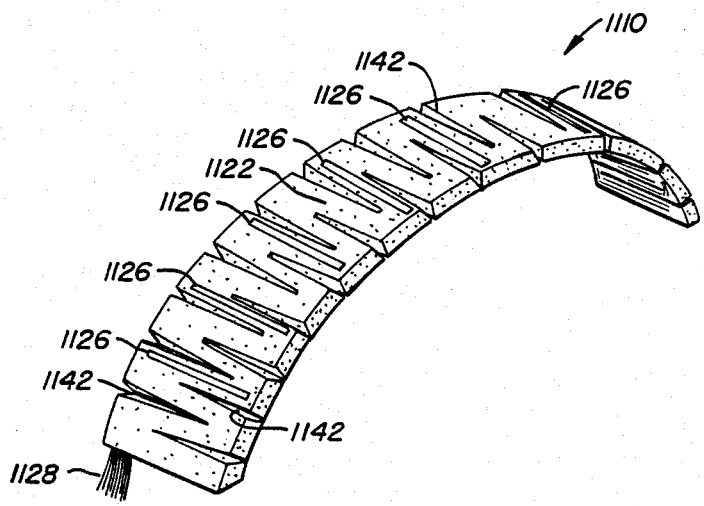
FIG._23.

MULTIPLE-ELECTRODE INTRACOCHLEAR DEVICE

This is a continuation of application Ser. No. 728,307 filed on Apr. 29, 1986 is now abandoned.

TECHNICAL FIELD

This invention relates to implantable intracochlear devices and more particularly, to an implantable intracochlear device that has a plurality of stimulating electrodes.

BACKGROUND ART

Implantable intracochlear, prosthetic devices have been used in recent years to stimulate auditory nerves so that a person suffering from certain types of deafness may hear. Such prior art devices include U.S. Pat. No. 3,449,768 and Canadian Patent No. 1,115,352.

The human ear can generally be categorized into the outer ear, the middle ear, and the inner ear. A substantial portion of the inner ear is the cochlea, which has a snail-like structure. The cochlea, filled with conductive fluids (perilymph in the scala vestibuli and the scala tympani and endolymph in the scala media) is positioned between the middle ear and auditory nerve endings, and transforms mechanical vibrations (sound) emanating from the middle ear into electrical, auditory nerve signals. Such a transformation is caused by the mechanical vibration of sensory hair cells, more than 15,000 of which are normally present in each cochlea. When these sensory hair cells are damaged, an implantable intracochlear device can be substituted to stimulate the undamaged nerve endings.

Auditory nerve endings are distributed along the entire length of the scala media (endotic space) segment of the cochlea. Those near the basal (larger) end are sensitive to high frequency sound and those near the apical (narrower) end are sensitive to low frequency sound. While exact positioning with respect to frequency is difficult to determine for any given patient or even a group of patients, it is known that beneficial results can be obtained if the electrodes have a predetermined spacing between them, i.e., a relative spacing. To fully duplicate normal hearing, as many of these nerve endings as possible should be stimulated. Accordingly, an implantable device having a plurality of electrodes may be used, each electrode being adapted to transmit over a different frequency band.

The ideal intracochlear device should exhibit a number of, sometimes conflicting, attributes. It should have multiple electrodes to provide a variety of stimulating frequencies. The device should be easy to insert, in that it must have the proper stiffness lengthwise and yet be laterally flexible in order to permit the device to follow the snail-shaped scala tympani section of the cochlea without damaging the sensitive tissue of the basilar membrane therein. This has proved to be a significant problem, and attempts to use solid, rubberized electrodes have not been fully successful because they must be preshaped to conform to the spiral shaped cochlea when they are fully inserted, thus making insertion difficult without trauma to the sensitive basilar membrane on which the organ of Corti rests. If scar tissue develops on the basilar membrane due to trauma, this can interfere with the transmission of electrical signals from the electrode to the auditory nerve cells and remaining hair cells.

Preferably, the device also should be tapered, which is the general configuration of the cochlea.

The device should be biologically inert and be capable of being implanted for long periods of time. The device should be easy to remove and be capable of leaving a tapered channel in which a replacement electrode may be inserted. It should be a "unitary" object where the electrodes are positioned at predetermined optimal spacings, permitting a surgeon to only insert or remove the entire device and not be concerned about the relative positioning of the electrodes during surgery. Further, the device should be capable of minimizing interfering signals.

DISCLOSURE OF THE INVENTION

In order to accomplish the above and still further objects, the present invention provides a cochlear device for electrically stimulating the auditory nerve of a patient at multiple points along the length of the cochlea so as to provide artificial hearing over a wide range of frequencies.

More particularly, the implantable intracochlear device comprises a plurality of substantially incompressible elements each of whose major surfaces are essentially parallel and substantially greater than its minor surfaces, with the elements being assembled adjacent and in contact with one another along a common axis to form a stack. The elements are resiliently attached together so that the stack of elements is stiff in compression along the common axis and is flexible in tension when the elements are forced to deviate from the common axis by the application of an external force.

A plurality of electrodes are supported by the stack at predetermined, spaced apart locations along its length and separate, electrically conductive wires carried by the stack are connected to each electrode to allow them to be electrically stimulated from outside of the cochlea.

In a preferred embodiment, the stack elements are comprised of the windings of a helical, flexible carrier coil. The carrier coil is covered with an electrically insulative, continuous sheath of a biologically-inert material and is wound sufficiently tight to form substantially hollow tube. The electrode wires are positioned within the carrier coil in an axially-extending fashion. The bare end of each of the plurality of conductive wires winds circumferentially about a different few of the carrier coil windings. Each of the electrodes, which are positioned at predetermined locations along the carrier coil, has an axis which is coincidental with that of the carrier coil.

The implantable intracochlear device also can comprise a generally spherical electrode positioned at the terminus of the carrier coil. The diameter of this terminus electrode can be equal to or a small amount greater than the diameter of the carrier helix to enhance the efficacious placement and removal of the implantable device. The spherical electrode is also connected via its own insulated conductive wire. Thus, each of the electrodes as well as the spherical electrode stimulates one of the multiple points along the length of the cochlea. The carrier coil can be a tapered toward the inner end.

Other embodiments of the present invention include electrodes in other forms, such as bare wire ends which wind about the carrier coil windings to form double helixes or the electrodes can be spherical in shape. Moreover, the carrier coil itself can, in some embodiments, include an internal electrically-conductive wire which functions as an electrical shield.

Other advantageous embodiments include a plurality of ring shaped elements held together in a stack along a common axis by an elastomeric bonding material or an elastic sleeve which fits over the stack. In still other embodiments, the stack elements are comprised of the segments formed by transverse, partial cuts in a rectangularly shaped plug of elastomeric material. The cuts alternate from side to side to allow the plug to flex laterally. The plug material is chosen to be relatively inelastic in compression. In still another embodiment, a plug of such material has a flat spring embedded in it. The plug is then formed into an arch shape along the common axis. In this embodiment, the "elements" making up the "stack" are the side to side portions of the flat spring.

In all embodiments, the electrodes are supported on the exterior surface of the stack of elements at spaced apart locations along its length. The individual wires, which are connected to the separate electrodes, are likewise carried by the stack. In some embodiments, these wires are actually traces of conductive material which are printed or deposited on the stack.

One advantage, common to all embodiments, of the present invention is that the implantable intracochlear device is easy to insert and to remove, having the requisite axial stiffness with lateral flexibility for placement into the snail-shaped cochlea.

A further advantage of the present invention is that the novel implantable intracochlear device is capable of stimulating the auditory nerve at multiple, spaced apart points along the length of the cochlea so as to provide artificial hearing over a wide range of frequencies.

Still another advantage of the present invention is that the novel implantable intracochlear device has electrodes which are spaced apart by predetermined lengths along the entire length of the device and form an integral part of it, permitting a surgeon to insert or remove the entire device without being concerned with the relative positioning of the electrodes.

Yet a further advantage of the present invention is that the implantable intracochlear device is biologically inert, permitting long-term implantation.

An additional advantage of some embodiments of the present invention is that interfering signals are minimized by having a carrier coil that can function as an electrical shield.

It is an object of the present invention to provide an implantable intracochlear device that is easily and non-traumatically insertable and removable, having a preferred tapered configuration as well as the requisite axial stiffness and lateral flexibility for placement into the snail-shaped cochlea.

It is another an object of the present invention to provide an implantable intracochlear device in which a plurality of electrodes are pre-positioned within the device and are a part of the entire, unitary device.

It is another object of the present invention to provide an implantable intracochlear device that is biologically inert.

It is a still further object of the present invention to provide an implantable intracochlear device that includes a carrier coil which is capable of functioning as an electrical shield.

Other objects, features, and advantages of the present invention will appear from the following detailed description of the best mode of a preferred embodiment, taken together with the accompanying drawings.

BRIEF DESCRIPTION OF THE DRAWINGS

FIG. 1 is a partial, exploded, perspective view of an implantable intracochlear device according to a first embodiment of the present invention;

FIG. 2 is a partial, exploded, perspective view of a second embodiment of the implantable intracochlear device of the present invention;

FIG. 3 is a partial, exploded, perspective view of a third embodiment of the implantable intracochlear device of the present invention;

FIG. 4 is an enlarged, partial, exploded, perspective view of a modification of the second embodiment of the implantable intracochlear device of the present invention;

FIG. 5 is a partial, enlarged, vertical view of the preferred embodiment of the implantable intracochlear device of the present invention;

FIG. 6 is a vertical view illustrating one of the steps in making the electrode illustrated in FIG. 1;

FIG. 7 is a vertical view, partly in section, illustrating apparatus for making the device depicted in FIG. 1;

FIGS. 8 and 9 are a perspective and cross-sectional view, respectively, of the mandrel used in making the device depicted in FIG. 1;

FIG. 10 is an enlarged, vertical, sectional view of a modification of the device depicted in FIG. 1;

FIGS. 11, 12, 13, 14 and 15 are each vertical, sectional views of additional embodiments of the invention;

FIG. 16 is a vertical, sectional view of a cochlea illustrating the positioning of the intracochlear device and its ability to conform to the contour of the cochlea;

FIG. 17 is a top plan view, with portions broken away and in section of still another form of the embodiment;

FIG. 18 is a perspective view of the embodiment in FIG. 17;

FIG. 19 is a side view of the embodiment depicted in FIG. 17 when it is flexed laterally;

FIG. 20 is a top plan view of a further embodiment of the invention;

FIG. 21 is a bottom plan view of the embodiment depicted in FIG. 20;

FIG. 22 is a sectional view taken generally along the lines 22—22 in FIG. 21; and FIG. 23 is a perspective view of the embodiment depicted in FIG. 20 when it is flexed laterally.

BEST MODE FOR CARRYING OUT THE INVENTION

Referring to FIG. 1, there is shown an implantable intracochlear device 10 comprised of a stack 12 of substantially incompressible, flat elements 22 which are arranged to be parallel in the direction of their thicknesses along a common longitudinal axis 5. The elements 22 are the windings of a helically wound, flexible coil 14. The stack 12 has an innermost terminus 16 which is intended to be positioned at the furthest distance into the cochlea. The coil 14 includes an internal electrically-conductive wire 18, and an external, biologically-inert, insulating sheath 20. Although the carrier coil 14 is manufactured as a relatively tightly-wound coil like coil 414 of FIG. 5, its windings 22, and the windings of the other embodiments depicted in FIGS. 2-4, inclusive, are illustrated as spaced apart in order to illustrate the positions of other elements of the device 10. In the preferred embodiment, the carrier coil 14 is a tapered helix, with the radius of one winding 22 being smaller than the radius of a preceding winding and larger than the radius of a succeeding winding, so that the device can be inserted into the cochlea, specifically the scala tympani channel, small end 16 first.

Like all of the embodiments to be described, the stack elements 22, i.e. the coil windings, when the coil is tightly wound, can be considered flat in that their major surfaces are essentialy parallel and substantially greater than their minor surfaces. Thus, with reference to FIG. 4, the portions L of the winding surfaces which are in contact with the next adjacent windings are parallel and are substantially greater than the surface portions W taken in the direction along the axis 5. Furthermore, because the windings 22 are formed from a continuous, resilient wire 18, they are, in effect, resiliently attached to each other.

This is an important concept to the invention. By having a series of flat, substantially incompressible elements 22 formed into a stack 12, the device of the invention has the property of stiffness in compression along the axis 5 but flexibility in tension when the elements 22 are forced to deviate from the common axis 5 by the application of an external force such as when the device is forced to follow the snail-shaped contour of the cochlea, as will be explained further in reference to FIG. 16.

The device 10 also comprises a plurality of electrodes 26 which are supported on the stack 12. Each electrode 26 is connected to an electrically-conductive wire 28 which is covered with a biologically inert, insulating sheath 30. The wire 28 and sheath 30 are positioned within the stack 12 in an axially-extending fashion. One bare end of the wire 28 winds about one carrier coil winding 22 to form one electrode 26 in the shape of a double helix. The electrodes 26 are positioned at predetermined locations along the stack 12. The device is intended primarily for unipolar operation. When installed in a patient, an additional contact with the patient's mastoid muscle or other grounding site provides a circuit ground to which all of the other electrodes 26 are referenced.

The device 10 further comprises a spherical terminus electrode 34 whose diameter approximates, and preferably slightly exceeds, the diameter of the carrier helix. An electrically conductive wire 36 is attached at one end to the spherical electrode 34 and is covered with an external, biologically-inert, insulating sheath 38. The wire 36 is also positioned within the stack 12 in an axially-extending fashion. The spherical coil 14 to ease the placement and removal of the implantable device 12. The internal wires 18, 28 and 36 are manufactured from a biologically-inert conductive material such as platinum, other inert materials such as platinum iridium or stainless steel can also be used. The external sheaths 20, 30 and 38 are manufactured from a biologically inert, non-conductive material such as polyfluorotetraethylene, sold under the trademark Teflon.

The dimensions of the device 10 are greatly enlarged in the figures for purposes of illustration. Its actual length is approximately 0.740 inch, with the larger end of the stack having a diameter of about 0.035 inch and the terminus 16 a diameter of about 0.020 inch. Each of the wires 18 and 28 has a diameter of about 0.001–0.002 inch. Each of the sheaths 20 and 30 has a thickness of about 0.001–0.002 inch. The spherical terminus electrode 34 has a diameter of about 0.022 inch.

The length of the electrode 26 can vary depending on the application. For example, each of the electrodes 26 in FIG. 1 winds about the entire length of one carrier coil winding 22. In FIG. 3, however, each electrode 226 winds about only a small portion of the carrier coil winding 222. Since the various embodiments disclosed in the present application include similar elements, the numerical designation for the similar elements are designated by providing a different prefix numeral. For example, the electrode for the device shown in FIG. 3 is designated as 226 whereas the electrode in FIG. 1 is designated 26.

As best shown in FIG. 2, in another embodiment of the present invention, the device 110 includes elements which are all identical to the corresponding elements in the embodiment shown in FIG. 1 with the exception that the electrodes 126 are all generally spherical electrodes as opposed to windings about the carrier coil windings 22. In this embodiment, each of the spherical electrodes 126 is positioned to protrude from between two carrier coil windings 122.

A modification of the second embodiment is disclosed in FIG. 4 wherein the carrier coil 314 does not include an internal electrically-conductive wire and is comprised of a nonconductive material.

A preferred embodiment of the present invention is shown in FIGS. 5 and 16. In this embodiment, the device 412 comprises a stack 412 made up of the windings 422 of a helical, flexible carrier coil 414, which has an innermost terminus 416. The carrier coil 414, manufactured from a biologically-inert material, is a plurality of tightly-wound windings 422 which define a hollow stack or tube. The tube can be tapered or cylindrical.

The device 410 also comprises a plurality of electrodes 426 carried by the stack 412. Each electrode 426 is made of an electrically-conductive wire 428 that is sheathed with a biologically-inert, insulating material 430. The wire 428 and sheath 430 are positioned within the stack 412 in an axially-extending fashion. A bare end of the wire 428 is wound circumferentially about a few windings 422 of the tubular carrier coil 414. The tip of the electrode 426 is tucked inbetween the windings 414. Thus, each of the helical electrodes 426, which are positioned at predetermined locations along the carrier coil 414, has an axis which is coincidental with the axis 5 of the carrier coil 414.

The device 410 can further comprise a spherical, terminus electrode 434. The spherical electrode 434 is connected to an electrically-conductive wire 436 that is covered with a biologically-inert, insulating sheath 438. The wire 436 and sheath 438 are also positioned within the stack or tube 412 in the axially-extending fashion. The spherical electrode 436 is positioned at the terminus 416.

As best illustrated in FIG. 16, the device 410, whether or not tapered, is surgically insertable into the scala tympani channel c of a cochlea. The channel c is relatively narrow, however, the helical configuration of the carrier coil 414 provides sufficient axial stiffness such that device 410 can be readily inserted. Since the cochlea is also snail-shaped (the channel within the cochlea is a tapered helix), the device must be capable of bending as it is being inserted into the scala tympani channel. Lateral flexibility comes from the carrier coil 414 with its plurality of windings 422.

It will be observed that the winding elements 422 are in compression and thus touch each other along the inner radius of curvature of the device 410 but are in tension along the outer radius of curvature and so are not in contact. This is because the winding elements 422 are compelled by the external force exerted by the walls of the cochlea on the winding elements 422 in a direction transverse to the axis 5 to become radially aligned to make the curve rather than be axially aligned along the axis 5. This lateral, flexible resilience characteristic is an important part of the invention. It keeps the device 410 pushed against the larger radius of curvature of the cochlea instead of allowing contact with the surface of the basilar membrane B where scar tissue or a tearing might interfere with transmission of the electrical signals to the auditory nerve cells in the organ of Corti.

The tapered configuration of the device 410 as well as the use of the spherical, terminus electrode 434 aids the insertion into the tapered scala tympani channel. When scar tissue or calcification occurs around an implanted device, the tapered helical configuration facilitates removal of the device 410. In extreme cases, the helical winding can simply be unwound by pulling lengthwise, thereby greatly reducing the diameter of the device.

The electrodes 426 are prepositioned on the carrier coil 414 so that the surgeon need not be concerned with the optimal spatial relationship of the electrodes 426 during surgery. Moreover, since the electrodes 426 are an integral part of the device 410, the surgeon is dealing only with one unitary object during insertion or removal.

Because the electrode 426 winds circumferentially about the carrier coil 414, the electrode 426 is capable of providing greater contact with the perilymph (conductive fluid) than the electrodes depicted in some of the other figures.

FIGS. 6-10 are illustrative of a method of manufacturing a device of the type shown in FIG. 1. In FIG. 6, the carrier helix 14 is shown straightened, before winding into a helix. An apparatus 500 can be used for manufacturing the device 10, as best shown in FIG. 7.

Apparatus 500 comprises a frame 502, a rotatable mandrel 504 mounted on the frame 502, a crank handle 508 that is attached to the mandrel 504 through a chuck 511 which grips one end of the mandrel 504. The crank handle 508 has its shaft thread mounted in the frame 502. A rotatable reel 510 is mounted on the frame 502 and is rotated through a bevel gear assembly 512 and a reel crank handle 514.

The mandrel 504, as best shown in FIGS. 8-10, has a plurality of axially extending grooves 516. A thin wire held in tension can be substituted for the mandrel.

The crank handle 508 has a plurality of gearing teeth 518 which cooperate with the gear teeth 506 of the frame 502 in the manner to be described. Mounted on the periphery of the reel 510 is a spool 520 of electrode wire 28 which is covered with the insulating sheath 30. A spool 522 of the carrier coil filament or wire 14 is also provided. In manufacturing the device 10, an end of the carrier wire 14 is attached to the mandrel 504, as best shown in FIGS. 7 and 8. The carrier wire spool 522 is weighted in order to keep the unreeled portion of the carrier wire 14 taut. A portion of the electrode wire 28, preferably with the end stripped of its insulating sheath 30, is attached to the carrier wire 14, as best shown in FIGS. 6 and 7. The reel crank handle 514 is then turned, causing the reel gear 512 to rotate the reel 510 on which the spool 520 of the electrode wire 28 is attached about the longitudinal axis of the carrier wire 14. The turning of the reel crank handle 514 results in the formation of a helical electrode 26. After the helical electrode 26 has been formed, a sufficient length of the electrode wire 28 with its sheath 30 is then selected and severed from the spool 520. This length of the electrode wire 28 is placed lengthwise against the mandrel, for example in one of the axially extending mandrel grooves 516, as best shown in FIGS. 8 and 9. Some tension is maintained on the electrode wire 28 to keep it in a groove 516 as well as to facilitate subsequent operations of the mandrel 504.

The mandrel crank handle 508 is then turned, causing the carrier wire 14 to wrap circumferentially about the mandrel 504, as best shown in FIG. 8. The rotation of the mandrel 504 creates the helical windings 22. The pitch of the gear teeth 506 and 518 are selected such that with each revolution of the mandrel 504 it is shifted axially by a distance equal to the diameter of the carrier wire 14. For a conical coil, a conical mandrel is used. A similar arrangement with obvious modifications can be used to make the other wire wound embodiments of the invention.

After the complete helical coil 14 is formed, the mandrel 504 is removed, leaving a hollow space within which the electrode wires 28 can slip as the coil bends to conform to the contour of the cochlea. If such slippage of the wires were not provided for, the device 10 would be laterally stiff.

In addition to the various embodiments described previously, another embodiment is illustrated in FIG. 11. The device 610 of FIG. 11 is a plurality of insulated, helically wound, carrier filament windings 622 interposed axially with a plurality of annular, conductive electrodes 626. The winding 622 can extend over or through the hollow of the electrodes 626. The illustrated carrier windings 622 can be made with or without an inner conductive wire 618. Each of the annular electrodes 626 is connected to a separate conductive wire 628 which is covered with an insulating sheath 630. The electrode wires 628 are positioned within the carrier windings 622 in an axially extending fashion. In the alternative, separate insulating annular rings or stack of rings (not shown) can be positioned between the annular electrodes 626 in place of the winding 622. The insulating rings can be manufactured from materials such as Teflon, biologically pure silicone rubber, or glass and be elastically bonded to each other by an adhesive.

The embodiment illustrated in FIG. 12 is a modification of the embodiment of FIG. 1 to provide bipolar stimulation as opposed to the monopolar stimulation of the embodiments depicted in the previously discussed figures. The embodiment of FIG. 12 is identical to the embodiment of FIG. 1 with the exception that some portions of the carrier coil insulating sheath 20 have been removed to create ground electrodes 40, some of which are located between the electrodes 26.

As shown in FIG. 13, a further embodiment of the present invention is illustrated. The device 710 of FIG. 13 is comprised of a plurality of electrode wires 728 each of which is covered with an insulating sheath 730. The electrode wires 728 are concentrically, helically wound to form the general physical configuration of the device 710. More particularly, a first electrode wire 728A is helically wound and is positioned with a portion of its sheath 730A removed to form a first helical electrode 726A. At a predetermined position on the first sheath 730A, a bare portion of a second electrode wire 728B is circumferentially wound about the first electrode sheath 730A to form a second electrode 726B. The remainder of the wire 728B is covered with an insulating sheath 730B. A succession of such electrodes 726A, 726B, 726C and 726D is thus formed. The successive circumferential windings of the electrode wires 728A, 728B, 728C and 728D create a tapered configuration for the device 710.

Still another embodiment is illustrated in FIG. 14. In this embodiment, a plurality of side by side, helically coiled electrode wires 828 form the device 810. More particularly, for example, electrode wires 828A, 828B, 828C and 828D are helically wound in side by side fashion to form a hollow tube 812. At a predetermined position, a portion of the first sheath 830A is removed to form a helical electrode 826A which is wound over the wires 828B, 828C and 828D. After the formation of the electrode 826A, the remaining electrode wires 828B, 828C and 828D continue to be helically wound in side by side fashion. At a second location along the length of the device 812, the sheath 830B is removed and the bare portion of the wire 828B is helically wrapped over the wires 828C and 828D to form a second electrode 826B. This process is repeated to create helical electrodes 826C and 826D.

Still another embodiment of the present invention is illustrated in FIG. 15. The device 910 is comprised of a plurality of discrete rings 942, stacked together with a plurality of interposed annular electrodes 926. A plurality of flexible webs 944 are attached to the circumference of the coils 942 and span the distance between them. Alternatively, the web 944 could be continuous between electrodes 926. Like FIG. 1, FIG. 15 is an exploded view showing the device expanded lengthwise for purposes of illustration, as though it were in tension. In use, it would be compressed, with the rings 942 closely adjacent one another. Each annular electrode 926 is attached to a separate electrode wire 928 which is positioned in an axially extending fashion inside the device 910. The annular electrodes 926 can be manufactured from platinum; the rings 942 manufactured from platinum covered with polytetrafluoroethane (Teflon); and web 944 manufactured from a biologically pure silicon rubber (Silastic) membrane.

All of the devices are manufactured from biologically-inert materials, so that they are capable of being implanted for long periods of time. In those embodiments in which the carrier coil includes an internal electrically-conductive wire such as wire 18, 118, or 218, the carrier coil also functions like the shield conductor of a coaxial cable, protecting the enclosed active elements from unwanted pickup of stray interfering signals from radio broadcasts, electrical appliances, etc.

Referring now more particularly to FIGS. 17, 18 and 19, still another embodiment of the invention is illustrated. In this form of the invention, the device 1010 is comprised of a rectangularly shaped strip of biologically clean silicone rubber of the type sold under the trademark "SILASTIC." Other suitable materials can also be used. Such a material as commonly sold is relatively compressible in all directions and thus would not have the required axial stiffness. In order to overcome this problem, a serpentined filament 1042 of incompressible material is embedded within the plug. The filament 1042 is comprised of a number of side-to-side lengths as illustrated in FIG. 17. In some embodiments, the filament can be a spring made of a biologically inert material such as platinum, platinum-iridium, or stainless steel. The filament 1042 can be round in cross-section or it can be a flat ribbon.

On the top surface of the plug 1010 are supported a plurality of strip electrodes 1026 at spaced apart locations along the length of the plug. These electrodes can be, for example, metallic foil or printed circuit or silk-screened tracings of electrically conductive material. Each electrode 1026 is connected through the plug 1010 to a separate electrode wire 1028. Each wire 1028 is covered with an electrically insulative, nonconductive sheath as in the other embodiments. The wires 1028 can, in some embodiments, be connected to a terminal pad which connects to the individual electrodes 1026 through separate printed circuit traces (not shown) on the bottom of the plug 1010.

When the filament 1042 is comprised of a flat ribbon of incompressible material, the device will have axial stiffness due to the incompressible side to side segments of the ribbon 1042 and yet will be able to flex laterally, similar to the embodiment shown in FIG. 23, to follow the contour of the cochlea.

In the those embodiments where the filament 1042 is not a flat ribbon, prior to insertion into the cochlea, the plug 1010 is formed into an arc shape along its longitudinal axis as illustrated in FIG. 18. During insertion into the cochlea, the hollow or concave form of the arc is oriented towards the inner radius of curvature of the cochlea so that the convex portion of the lug conforms to the concave contour of the outer radius of curvature of the cochlea C. The combination of the filament 1042 and the arc shape give the plug 1010 the required axial stiffness coupled with lateral flexibility to enable it to safely negotiate the contours of the cochlea without damaging the delicate tissues on the inner radius, i.e. the basilar membrane.

Referring now more particularly to FIGS. 20-23, still another plug form of the embodiment is illustrated. In this embodiment, a plug 1110 of elastomeric material, such as biologically clean silicone rubber sold under the trademark "SILASTIC," is utilized. In this embodiment, however, the rubber is formed to be relatively inelastic and thus substantially incompressible compared to the plug illustrated in FIG. 17. Thus, the plug 1110 has axial stiffness. In order to provide for lateral flexibility, however, a series of partial slits 1142 are made through the thickness of the plug 1110 and approximately two thirds to three quarters of its width. The slits alternate from side to side, as illustrated in FIG. 20. In this way, the plug essentially acts like a serpentine spring with the portions of the plug material residing between the slits 1142 corresponding to the side-to-side portions of the filament 1042 of the embodiment illustrated in FIG. 17.

When the plug is flexed, as illustrated in FIG. 23, the top eges of the slits 1142, that is the portions of the slits which are at the outermost radius, will separate compared to the bottom edges of the slits, that is those at the innermost radius of curvature which will be compressed. This allows the plug 1110 to have lateral flexibility while still maintaining axial stiffness.

Like the embodiment of FIG. 17, the plug 1110 has a plurality of spaced apart electrodes 1126 which are printed, silk-screened, or otherwise deposited upon the top surface of the plug. The electrodes 1126 are made of an electrode conductive material such as foil or a tracing of conductive material. Again, the material should be chosen to be biologically inert.

As illustrated in FIG. 21, separate electrode wires 1128 attach to series of pads on the bottom of plug 1110 which are connected by means of tracings 1128A, 1128B . . . 1128G which connect through the plug 1110 to the separate electrodes 1126. It will be noted that only a few of the tracings 1128A through G are illustrated for sake of clarity. The tracings are patterned to avoid the slits 1142 and are covered with an insulating material.

While the embodiments depicted in FIGS. 17-23, inclusive, may appear very dissimilar to the embodiments depicted in the remaining figures, all of the embodiments have certain common features. They are all comprised of a stack of substantially incompressible, more or less flat elements which are stacked adjacent and in contact with one another along a common axis. By "flat" is meant that the major surfaces of the elements are essentially parallel and substantially greater than the minor surfaces. In the embodiments depicted in FIGS. 1-5, 11, 12, 13, and 14, the elements are the windings of the coils, the carrier or the electrode wires and the "stack" is the tube formed by the tight helical windings. The windings are resiliently connected together by portions of the carrier wire or filament (FIGS. 1-5, 11, 12) or the electrode wires (FIGS. 13, 14). In the embodiment shown in FIGS. 17-19, the elements are the portions of the plugs 1010 between the side to side segments of the filament 1042 and the filament segments. The resilient connection between the elements are the connecting portions of the plugs 1010 and the filament 1042 at the side edges of the plugs. In the embodiment shown in FIGS. 20-23, the elements are the plug portions between the slits 1142 and the resilient connections between the elements are the side portions of the plug.

This construction gives all of the embodiments axial stiffness in compression along the longitudinal axis and lateral flexibility when the structure is caused to deviate from this axis, thereby putting a part of the resilient connection between the elements in tension. Electrodes in all of the embodiments are supported at spaced apart locations along the longitudinal axis of the structure.

While various features of the invention have been disclosed and described in reference to particular embodiments, it should be apparent that some or all of these features can be used or substituted in the other embodiments. Thus, for example, the carrier coil 414, in applications which allow a stiffer coil, can have an inner conductor such as conductor 18 or 118 which is connected to the circuit ground to act as a coaxial shield for the conductors 428 and 436. In still other embodiments, the terminus spheres 34, 134, 234, 334 or 434 can be omitted.

Furthermore, while the above described electrodes are intended preferably for unipolar stimulation, in some embodiments, the electrodes can be connected to operate in pairs for bipolar stimulation. The term "wire" as used in this description and the claims is intended to apply to any filament-like conductor including, for example, a printed circuit trace.

Only a few of the several electrodes are shown in each embodiment. The applicant has successfully implanted devices of this type with as many as six electrodes, however, future devices will probably have even more electrodes.

It will be apparent to those skilled in the art that various modifications may be made within the spirit of the invention and the scope of the appended claims.

I claim:

1. An electrical stimulation device which is axially stiff and laterally flexible comprising:
   a plurality of substantially incompressible windings of a helically wound flexible coil, the windings being assembled adjacent and in contact with one another along a common axis to form a stack of windings, the stack of windings being stiff in compression along the common axis and being flexible in tension when the windings are forced to deviate from the common axis by the application of an external force,
   a plurality of electrodes supported by the stack of windings at predetermined, spaced apart locations along the stack of windings, and
   a plurality of electrically conductive wires carried by the stack of windings, the plurality of wires being electrically isolated from one another, each wire having one end which connects to a separate one of the electrodes and each wire further having a continuous, electrically insulative, biologically inert sheath,
   whereby each of the plurality of electrodes is independently operable to thereby provide electrical stimulation at multiple points along the stack of windings.

2. A stimulation device as claimed in claim 1 wherein the windings comprise a continuous filament which is tightly wound into a hollow tube.

3. A stimulation device as claimed in claim 1 wherein the dimensions of the windings taken perpendicular to the common axis decrease toward one end of the stack of windings so that the stack of windings is conically shaped.

4. A stimulation device as claimed in claim 1, further comprising
   an additional, spherically shaped terminus electrode positioned at a first end of the stack of windings and wherein a separate one of the sheathed wires is connected to the terminus electrode.

5. A stimulation device as claimed in claim 4 wherien the diameter of the terminus electrode is at least as large as the diameter of the stack of windings at the first end.

6. A stimulation device as claimed in claim 1 wherein the windings are hollow and the wires are carried within the stack of windings.

7. A stimulation device as claimed in claims 1, 2, 3, 4 or 6 wherein
   each of the plurality of electrodes comprises a sphere of conductive material.

8. A stimulation device as claimed in claim 6 further comprising an insulated conductive wire formed in a helix and positioned longitudinally inside the stack of windings to act as a coaxial, electrical shield against electrical noise signals for the electrode wires.

9. A stimulation device as claimed in claim 1 wherein the windings comprise an insulated, electrically conductive wire which is tightly wound in a helix to form a hollow tube.

10. An electrical stimulation device comprising
    a hollow, axially stiff and laterally flexible carrier tube having an exterior surface made of an electrically insulative, biologically inert material,
    a plurality of electrodes supported by the carrier tube at predetermined, spaced apart locations along its length, and
    a plurality of electrically conductive wires carried in the hollow of the carrier tube, the plurality of wires being electrically isolated from one another, each wire having one end which connects to a separate one of the electrodes and each wire further having a continuous, electrically insulative, biologically inert sheath, whereby each of the plurality of electrodes is independently operable to thereby provide electrical stimulation at multiple points along the length of the carrier tube.

11. A stimulation device as claimed in claim 10 wherein the carrier tube comprises a continuous filament which is tightly wound into a hollow tube.

12. A stimulation device as claimed in claim 10 wherein
the carrier tube is conically shaped.

13. A stimulation device as claimed in claim 10, further comprising
a spherically shaped terminus electrode positioned at a first end of the carrier tube and wherein a separate one of the sheathed wires is connected to the terminus electrode.

14. A stimulation device as claimed in claim 13 wherein
the diameter of the terminus electrode is at least as large as the diameter of the carrier tube at the first end.

15. A stimulation device as claimed in claims 10, 11, 12 or 14 wherein
each of the plurality of electrodes comprises a sphere of conductive material.

16. A stimulation device as claimed in claims 10, 11, 12 or 14 wherein the carrier comprises an insulated conductive wire formed in a helix and positioned longitudinally inside the carrier tube to act as a coaxial, electrical shield against electrical noise signals for the electrode wires.

17. A stimulation device as claimed in claim 10 wherein
the carrier tube comprises an insulated, electrically conductive wire which is tightly wound in a helix to form a hollow tube.

18. A cochlear device for electrically stimulating the auditory nerve of a patient at multiple points along the length of the cochlea, the device comprising
a helical carrier, the carrier having a continuous filament which is tightly wound into a hollow which is axially stiff and laterally flexible,
the filament having a continuous exterior surface made of an electrically insulative, biologically inert material;
a plurality of electrodes supported on the exterior surface of the carrier tube at predetermined, spaced apart locations along its length, and
a plurality of electrically conductive wires carried in the hollow of the carrier tube, the plurality of wires being electrically isolated from one another, each wire having one end which extends out between one or more windings of the carrier filament to connect to a separate one of the electrodes and the wire further having a continuous, electrically insulative, biologically inert sheath,
whereby each of the plurality of electrodes is independently operable to thereby provide electrical stimulation to the auditory nerve at multiple points along the length of the cochlea.

19. The cochlear device as claimed in claim 18, wherein
each of the plurality of electrodes comprises a sphere of conductive material.

20. The cochlear device as claimed in claim 18, wherein
the carrier comprises a conductive wire positioned longitudinally inside the filament whereby the carrier helix additionally acts as a coaxial, electrical shield against electrical noise signals for the electrode wires.

21. The cochlear device as claimed in claim 18, 19, or 20, wherein
the carrier helix is conically shaped.

22. The cochlear device as claimed in claim 21, further comprising
a spherically shaped terminus electrode positioned at a first end of the carrier helix and wherein separate one of the sheathed wires is connected to the terminus electrode.

23. The cochlear device as claimed in claims 18, 19 or 20, further comprising
a spherically shaped terminus electrode positioned at a first end of the carrier helix and wherein a separate one of the sheathed wires is connected to the terminus electrode.

24. The cochlear device as claimed in claim 23, wherein
the diameter of the terminus electrode is at least as large as the diameter of the carrier helix at the first end.

* * * * *

UNITED STATES PATENT AND TRADEMARK OFFICE
CERTIFICATE OF CORRECTION

PATENT NO. : 4,832,051

DATED : May 23, 1989

INVENTOR(S) : Jarvik, Robert K and Campbell, Patrick K.

It is certified that error appears in the above-identified patent and that said Letters Patent is hereby corrected as shown below:

On the title page Insert

--(73) Assignee: Symbion, Inc.
Salt Lake City, Utah --.

Signed and Sealed this

Twenty-fourth Day of October, 1989

Attest:

DONALD J. QUIGG

Attesting Officer

Commissioner of Patents and Trademarks